(12) United States Patent
Hitzeroth et al.

(10) Patent No.: US 11,857,251 B2
(45) Date of Patent: Jan. 2, 2024

(54) FLEXIBLE CIRCUIT FOR USE WITH A CATHETER AND RELATED MANUFACTURING METHOD

(71) Applicant: Biosense Webster (Israel) Ltd., Yokneam (IL)

(72) Inventors: Matthew Hitzeroth, Irwindale, CA (US); Daniele Ghidoli, Irwindale, CA (US); Steven Daniel, Irwindale, CA (US); Corey Rousu, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 562 days.

(21) Appl. No.: 17/094,915

(22) Filed: Nov. 11, 2020

(65) Prior Publication Data

US 2021/0177507 A1    Jun. 17, 2021

Related U.S. Application Data

(60) Provisional application No. 62/948,708, filed on Dec. 16, 2019.

(51) Int. Cl.
| | |
|---|---|
| A61B 5/00 | (2006.01) |
| A61B 5/287 | (2021.01) |
| A61B 18/14 | (2006.01) |
| A61B 8/00 | (2006.01) |
| A61B 5/367 | (2021.01) |
| A61B 18/00 | (2006.01) |

(52) U.S. Cl.
CPC .......... *A61B 18/1492* (2013.01); *A61B 5/287* (2021.01); *A61B 5/367* (2021.01); *A61B 8/4494* (2013.01); *A61B 2018/00351* (2013.01); *A61B 2018/00577* (2013.01)

(58) Field of Classification Search
CPC ........... A61B 5/25; A61B 5/271; A61B 5/283; A61B 2562/164; A61B 18/14; A61B 18/1492

See application file for complete search history.

(56) References Cited

U.S. PATENT DOCUMENTS

| | | | |
|---|---|---|---|
| 6,171,275 B1 | 1/2001 | Webster, Jr. | |
| 6,226,542 B1 | 5/2001 | Reisfeld | |
| 6,301,496 B1 | 10/2001 | Reisfeld | |
| 6,814,733 B2 | 11/2004 | Schwartz et al. | |

(Continued)

FOREIGN PATENT DOCUMENTS

EP    3199118 A1    8/2017

OTHER PUBLICATIONS

Extended European Search Report dated May 18, 2021, from corresponding European Application No. 20214257.6.

*Primary Examiner* — Eun Hwa Kim
(74) *Attorney, Agent, or Firm* — Troutman Pepper Hamilton Sanders LLP

(57) ABSTRACT

A flexible circuit including a first segment including a base section of the flexible circuit; a second segment including a lateral wall section; a transition section between the base and lateral wall sections, the transition section being at least partially positioned adjacent a shared region of the base and lateral wall sections; and one or more electrode regions including a respective electrode, the one or more electrode regions being positioned at least partially in the transition section and the second segment.

9 Claims, 10 Drawing Sheets

(56) References Cited

U.S. PATENT DOCUMENTS

| | | | |
|---|---|---|---|
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 7,536,218 B2 | 5/2009 | Govari et al. | |
| 7,756,576 B2 | 7/2010 | Levin | |
| 2007/0219551 A1* | 9/2007 | Honour | A61B 5/6852 606/41 |
| 2016/0128765 A1* | 5/2016 | Schultz | A61B 18/1492 606/41 |
| 2018/0071016 A1 | 3/2018 | Bar-Tal et al. | |
| 2018/0092688 A1* | 4/2018 | Tegg | A61B 18/18 |
| 2018/0110562 A1* | 4/2018 | Govari | A61B 5/036 |
| 2018/0256247 A1 | 9/2018 | Govari et al. | |
| 2020/0015693 A1 | 1/2020 | Beeckler et al. | |

\* cited by examiner

FLEXIBLE CIRCUIT FOR USE WITH A CATHETER AND RELATED MANUFACTURING METHOD

CROSS-REFERENCE TO RELATED APPLICATIONS

This application claims priority to U.S. provisional patent application No. 62/948,708 filed Dec. 16, 2019, the contents of which are incorporated herein by reference in their entirety as if set forth verbatim.

FIELD

The present disclosure relates generally to electrophysiology catheters and more particularly to a flexible-circuit for a split-tip catheter for use in electrocardiology ablation and mapping procedures.

BACKGROUND

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to block or modify the propagation of unwanted electrical signals from one portion of the heart to another. The ablation process destroys the unwanted electrical pathways by formation of non-conducting lesions.

SUMMARY

Accordingly, the inventors of this disclosure have recognized that there is a need for manufacturing multiple catheter tips at once with one or more removable inserts or molds that would be electroplated to create a dome. Many inserts could be processed at once depending on the size In some examples, a flexible circuit for use with a catheter tip is disclosed. The flexible circuit can include a first segment comprising a base section of; a second segment comprising a lateral wall section; a transition section between the base and lateral wall sections, the transition section being at least partially positioned adjacent a shared region of the base and lateral wall sections; and one or more electrode regions comprising a respective electrode, the one or more electrode regions being positioned at least partially in the transition section and the second segment.

In some examples, the first segment and/or second segment is generally planar when oriented in a planar configuration prior to being in the non-planar configuration when used with the catheter tip.

In some examples, the respective electrode of the one or more electrode regions is an ablating electrode.

In some examples, the respective electrode of the one or more electrode regions is a recording electrode.

In some examples, the respective electrode of the one or more electrode regions is a sensing electrode.

In some examples, the respective electrode of the one or more electrode regions.

In some examples, each of the one or more electrode regions comprises the electrode.

In some examples, the first segment has a generally circular shape when oriented in a planar configuration prior to being in the non-planar configuration when used with the catheter tip.

In some examples, the first segment has a diameter less than a diameter of the lateral wall sections formed by the second segment when oriented in a non-planar configuration; and the transition section has a dome-like shape that transitions between the lateral wall sections and the base section.

In some examples, the second segment is generally rectangular when oriented in a planar configuration prior to being in the non-planar configuration when used with the catheter tip and further includes a first sector, a second sector, and a third sector, each sector comprising a respective electrode region comprising an electrode, the respective electrode region being positioned at least partially in the transition section and the respective sector.

In some examples, the second sector is positioned between the first and second sectors and formed continuous with the first segment along an adjoining region.

In some examples, each sector has a rounded or curved upper edge that forms a dome-like shape to the transition section when the flexible circuit is in a non-planar configuration.

In some examples, the first segment has a plurality of triangle shaped sectors formed continuous with the first, second, and third sectors, respectively, of the second segment.

In some examples, each sector of the second segment has a rounded or curved upper edge that tapers from an upper edge of the respective sector of the second segment towards an apex of the respective triangle shaped sector.

In some examples, the base section is collectively formed by the triangle shaped sectors.

In some examples, at least one of the triangle shaped sectors has a first layer comprising a substrate; and a second layer that has a first upper petal adjacent an upper edge and the transition section; and a lower tab spaced apart from the first upper petal and extended substantially downward along a lateral edge of the respective sector.

In some examples, the second segment includes a plurality of rectangular shaped petal sectors radially separated about the first segment, each sector comprising a respective electrode regions comprising an electrode, the respective electrode regions being positioned at least partially in the transition section and the respective sector.

In some examples, the first segment is generally circular when oriented in a planar configuration prior to being in the non-planar configuration when used with the catheter tip.

In some examples, each sector has a rounded or curved upper edge that forms a dome-like shape to the transition section when the flexible circuit is in a non-planar configuration.

In some examples, each sector is foldable at or about a demarcation between the respective transition section and lateral wall section.

In some examples, each lateral edge of a respective sector is attachable to lateral edges of another of the sectors along a respective opposing lateral edge to form a cylindrical lateral wall section of in a non-planar configuration.

In some examples, each sector is radially spaced equally.

In some examples, the flexible circuit consists of only three sectors.

In some examples, the first segment includes a first layer comprising a substrate; and a second layer comprising a plurality of petals positioned adjacent or about the first segment, the plurality of petals being separated by one or more spaces.

In some examples, the petals are radially separated around a periphery of the first segment.

In some examples, an insulation layer is positioned with the one or more spaces.

In some examples, the first sector, the second sector, and the third sector each has a respective solder region comprising one or more contacts operatively coupled to a respective electrode.

In some examples, the first segment has a first-segment substrate and a first-segment insulator.

In some examples, one or both first and second segments has a plurality of selectively positioned irrigation ports.

In some examples, an insulator layer is included having polyamide, polyimide, liquid crystal polymer, or polyurethane.

In some examples, a catheter is disclosed for an elongate catheter body comprising at least one lumen; and a flexible circuit connected to a distal end of the elongate catheter body, the flexible circuit has a first segment comprising a base section of the tip; a second segment comprising a lateral wall section of the tip; a transition section between the base and lateral wall sections, the transition section being at least partially positioned adjacent a shared region of the base and lateral wall sections; and one or more electrode regions comprising a respective electrode, the one or more electrode regions being positioned at least partially in the transition section and the second segment.

In some examples, the first segment has a generally circular shape when oriented in a planar configuration.

In some examples, the first segment has a diameter less than a diameter of the lateral wall sections formed by the second segment when oriented in a non-planar configuration; and the transition section comprising a dome-like shape that transitions between the lateral wall sections and the base section.

In some examples, the second segment is generally rectangular when oriented in a planar configuration prior to being in the non-planar configuration and further includes a first sector, a second sector, and a third sector, each sector comprising a respective electrode region configured for an electrode, the respective electrode region being positioned at least partially in the transition section and the respective sector.

In some examples, the second sector is positioned between the first and second sectors and formed continuous with the first segment along an adjoining region.

In some examples, each sector has a rounded or curved upper edge that forms a dome-like shape to the transition section when the flexible circuit is in a non-planar configuration.

In some examples, the first segment has a plurality of triangle shaped sectors formed continuous with the first, second, and third sectors, respectively, of the second segment.

In some examples, each sector of the second segment has a rounded or curved upper edge that tapers from an upper edge of the respective sector of the second segment towards an apex of the respective triangle shaped sector.

In some examples, the base section of the tip is collectively formed by the triangle shaped sectors.

In some examples, at least one of the triangle shaped sectors includes a first layer comprising a substrate; and a second layer which includes a first upper petal adjacent an upper edge and the transition section; and a lower tab spaced apart from the first upper petal and extended substantially downward along a lateral edge of the respective sector.

In some examples, the second segment has a plurality of rectangular shaped petal sectors radially separated about the first segment, each sector has a respective electrode region configured for an electrode, the respective electrode regions being positioned at least partially in the transition section and the respective sector.

In some examples, the first segment is generally circular when oriented in a planar configuration.

In some examples, each sector comprising a rounded or curved upper edge that forms a dome-like shape to the transition section when the flexible circuit is in a non-planar configuration.

In some examples, each sector being foldable at or about a demarcation between the respective transition section and lateral wall section.

In some examples, each lateral edge of a respective sector being attachable to lateral edges of another of the sectors along a respective opposing lateral edge to form a cylindrical lateral wall section of in a non-planar configuration.

In some examples, each sector being radially spaced equally.

In some examples, the catheter consists of only three sectors.

In some examples, the first segment includes a first layer comprising a substrate; and a second layer comprising a plurality of petals positioned adjacent or about the first segment, the plurality of petals being separated by one or more spaces.

In some examples, an insulation layer is positioned with the one or more spaces.

In some examples, the petals are radially separated around a periphery of the first segment.

In some examples, the first sector, the second sector, and the third sector each comprise a respective solder region has one or more contacts operatively coupled to a respective electrode.

In some examples, the first segment has a first-segment substrate and a first-segment insulator.

In some examples, one or both first and second segments has a plurality of selectively positioned irrigation ports.

In some examples, an insulator layer is included with polyamide, polyimide, liquid crystal polymer, or polyurethane.

In some examples, a method of assembling a catheter is disclosed. The method includes changing a planar configuration of a flexible circuit for a catheter tip to a non-planar configuration, the flexible circuit having a first segment comprising a base section; a second segment comprising a lateral wall section; a transition section between the base and lateral wall sections, the transition section being at least partially positioned adjacent a shared region of the base and lateral wall sections; and one or more electrode regions configured for a respective electrode to ablate tissue, the one or more electrode regions being positioned at least partially in the transition section and the second segment. The method includes connecting a proximal end opposite the base section of the second segment in the non-planar configuration to a distal end of an elongate catheter body.

In some examples, the non-planar configuration has a cylindrical configuration.

In some examples, the method includes positioning an electrode with each of the one or more electrode regions. The electrode can be an ablation electrode, a sensing electrode, a recording electrode, and/or the like.

In some examples, the method includes forming the first segment with a generally circular shape when oriented in the planar configuration.

In some examples, the method includes forming the first segment comprising a diameter less than a diameter of the lateral wall sections of the second segment in the non-planar configuration; and forming the transition section with a dome-like shape that transitions between the lateral wall sections and the base section.

In some examples, the method includes forming the second segment in a generally rectangular shape in the planar configuration and comprising a first sector, a second sector, and a third sector, each sector comprising a respective electrode region configured for an electrode to ablate tissue, the respective electrode regions being positioned at least partially in the transition section and the respective sector.

In some examples, the method includes connecting lead wires to ablation electrodes of each of the first sector, the second sector, and the third sector.

In some examples, the method includes positioning the second sector between the first and second sectors and continuous with the first segment along and adjoining region.

In some examples, the method includes forming the first segment with a plurality of triangle shaped sectors continuous with the first, second, and third sectors, respectively, of the second segment.

In some examples, each sector of the second segment has a rounded or curved upper edge that tapers from an upper edge of the respective sector of the second segment towards an apex of the respective triangle shaped sector.

In some examples, the method includes forming the base section of the tip is with each of the triangle shaped sectors.

In some examples, at least one of the triangle shaped sectors includes a first layer comprising a substrate; and a second layer that includes a first upper petal adjacent an upper edge and the transition section; and a lower tab spaced apart from the first upper petal and extended substantially downward along a lateral edge of the respective sector.

In some examples, the method includes forming the second segment with a plurality of rectangular shaped petal sectors radially separated about the first segment, each sector comprising a respective electrode regions configured for an electrode to ablate tissue, the respective electrode regions being positioned at least partially in the transition section and the respective sector.

In some examples, the method includes forming the first segment in a generally circular shape when oriented in the planar configuration.

In some examples, the method includes rounding or curving an upper edge of the second segment that forms a dome-like shape to the transition section when the flexible circuit is in the non-planar configuration.

In some examples, the method includes folding each sector being at or about a demarcation between the respective transition section and lateral wall section to move the second segment to the non-planar configuration.

In some examples, the method includes attaching each lateral edge of a respective sector to lateral edges of another of the sectors along a respective opposing lateral edge to form a cylindrical lateral wall section of in the non-planar configuration.

In some examples, the method includes equally radially spacing each sector about the first segment.

In some examples, each sector has a rounded or curved upper edge that forms a dome-like shape to the transition section when the flexible circuit is in a non-planar configuration.

In some examples, a first layer is included with a substrate; and a second layer comprising a plurality of petals positioned adjacent or about the first segment, the plurality of petals being separated by one or more spaces.

In some examples, an insulation layer is positioned with the one or more spaces.

In some examples, the first sector, the second sector, and the third sector each have a respective solder region comprising one or more contacts operatively coupled to a respective electrode.

In some examples, the first segment has a first-segment substrate and a first-segment insulator.

In some examples, the method includes selectively positioning a plurality of irrigation ports with the first and/or second segments.

In some examples, a method of ablating tissue is disclosed. The method includes inserting any catheter according to the preceding example into a subject; contacting the flexible circuit of the catheter to cardiac tissue; and ablating, with the flexible circuit, tissue.

The present disclosure will be more fully understood from the following detailed description of embodiments thereof, taken together with the drawings.

BRIEF DESCRIPTION OF THE DRAWINGS

While the specification concludes with claims, which particularly point out and distinctly claim the subject matter described herein, it is believed the subject matter will be better understood from the following description in conjunction with the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation.

DETAILED DESCRIPTION

As used herein, the terms "insulator," "insulation material," "insulative material," and the like, each connote materials and structures comprising at least one material that has properties, generally accepted by those of skill in the art, to resist transfer of heat and conveyance of electrical signals. Such materials include, but are not limited to, polyamide, polyimide, polyurethane, polycarbonate, ceramic, liquid crystal polymer, and high-temperature epoxy.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As used herein, a "subject" or "patient" may refer to any applicable human patient as well as any mammal, veterinarian animal, livestock animal or pet type animal, etc. As an example, the animal may be a laboratory animal specifically selected to have certain characteristics similar to a human (e.g., rat, dog, pig, rabbit, monkey, or the like).

As used herein, "operator" may include a doctor, surgeon, or any other individual or instrumentation associated with the medical procedure used with the device(s) of this disclosure.

Ablation, particularly of cardiac tissue, depends upon accurate delivery of ablative energy while avoiding negative side effects caused by providing ablative energy to blood such as thrombus formation. A catheter having a tip divided into three segments directed to these purposes is disclosed.

Figure 1:
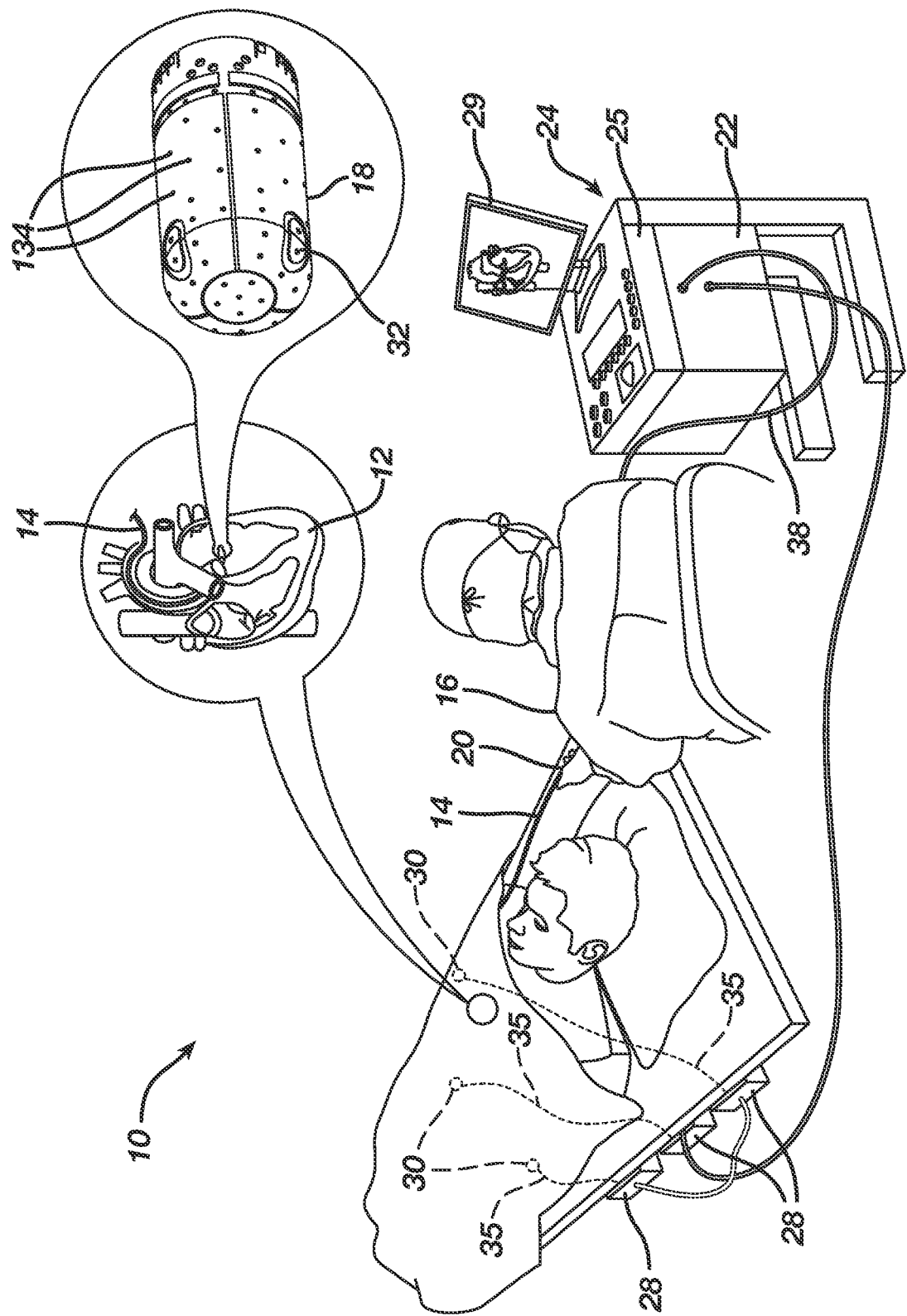
FIG. 1 depicts a system for evaluating electrical activity in a heart of a living subject and providing treatment thereto using a catheter.

FIG. 1 depicts a system 10 for evaluating electrical activity and performing ablative procedures on a heart 12 of a living subject. The system includes a diagnostic/therapeutic catheter having a catheter body 14 having a distal end 15 and a tip, e.g., tip 18 disposed thereon, which may be percutaneously inserted by an operator 16 through the patient's vascular system into a chamber or vascular structure of the heart 12. The operator 16, who is typically a physician, brings the catheter's tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference in their entirety. One commercial product embodying elements of system 10 is available as the CARTO® 3 System, available from Biosense Webster, Inc., 33 Technology Drive, Irvine, CA 92618.

Areas determined to be abnormal, for example by evaluation of the electrical activation maps, can be ablated by application of thermal energy, e.g., by passage of radiofrequency electrical current through wires in the catheter to one or more electrodes at the tip 18, which apply the radiofrequency energy to target tissue. The energy is absorbed in the tissue, heating it to a point (typically above 50° C.) at which point it permanently loses its electrical excitability. This procedure creates non-conducting lesions in the cardiac tissue, which disrupt the abnormal electrical pathway causing the arrhythmia. Such principles can be applied to different heart chambers to diagnose and treat many different types of cardiac arrhythmias.

The catheter typically includes a handle 20, having suitable controls on the handle to enable the operator 16 to steer, position and orient the distal end 15 of the catheter as desired for the ablation. Ablation energy and electrical signals can be conveyed to and from the heart 12 through one or more electrodes 32 located at or near the tip 18, or comprising tip 18, via cable 38 to the console 24. Pacing signals and other control signals may be conveyed from the console 24 through the cable 38 and the electrodes 32 to the heart 12. Wire connections 35 link the console 24 with body surface electrodes 30 and other components of a positioning subsystem for measuring location and orientation coordinates of the catheter. The processor 22 or another processor may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference in its entirety. At least one temperature sensor, typically a thermocouple or thermistor, may be included on or near each of the electrodes 32, as will be detailed below.

The console 24 typically contains one or more ablation power generators 25. The catheter may be adapted to conduct ablative energy to the heart using any known ablation technique, e.g., radiofrequency energy, ultrasound energy, cryogenic energy, and laser-produced light energy. Such methods are disclosed in commonly assigned U.S. Pat. Nos. 6,814,733, 6,997,924, and 7,156,816, which are herein incorporated by reference in their entirety.

The positioning subsystem may also include a magnetic position tracking arrangement that determines the position and orientation of the catheter by generating magnetic fields in a predefined working volume and sensing these fields at the catheter, using coils or traces disposed within the catheter, typically proximate to the tip. A positioning subsystem is described in U.S. Pat. No. 7,756,576, which is hereby incorporated by reference in its entirety, and in the above-noted U.S. Pat. No. 7,536,218. Operator 16 may observe and regulate the functions of the catheter via console 24. Console 24 includes a processor, preferably a computer with appropriate signal processing circuits. The processor is coupled to drive a monitor 29. The signal processing circuits typically receive, amplify, filter and digitize signals from the catheter, including signals generated by sensors, e.g., electrodes 32, such as electrical and temperature sensors, and a plurality of location sensing coils or traces located distally in the catheter. The digitized signals are received and used by the console 24 and the positioning system to compute the position and orientation of the catheter, and to analyze the electrical signals received from the catheter.

The subject matter disclosed herein concerns improvements to fabrication and functionality of catheter tips known in the art, such as that disclosed in U.S. Pat. No. 6,171,275 to Webster, which is incorporated herein by reference in its entirety. The improved catheter tip may be fabricated via a lithographic process as a planar flexible circuit 100 reflected in FIGS. 2-4. The flexible circuit 100 is, as its description suggests, flexible, meaning it can be bent into various non-planar configurations. For example, the configuration may be changed from planar to cylindrical, such that flexible circuit 100 may be changed into a cylindrical flexible-circuit flexible circuit 200, reflected in FIG. 5. Accordingly, apart from the planar configuration of flexible circuit 100 and the non-planar configuration of flexible circuit 200, it should be understood that features described herein with respect to flexible circuit 100 are also present in flexible circuit 200 and, similarly, features described herein with respect to flexible circuit 200 are also present in flexible circuit 100, even if express disclosure is not made concerning one of these configurations. Further, the surface of flexible circuit 100 visible in FIGS. 2-4 becomes flexible circuit 200 of FIG. 5.

Figure 2:
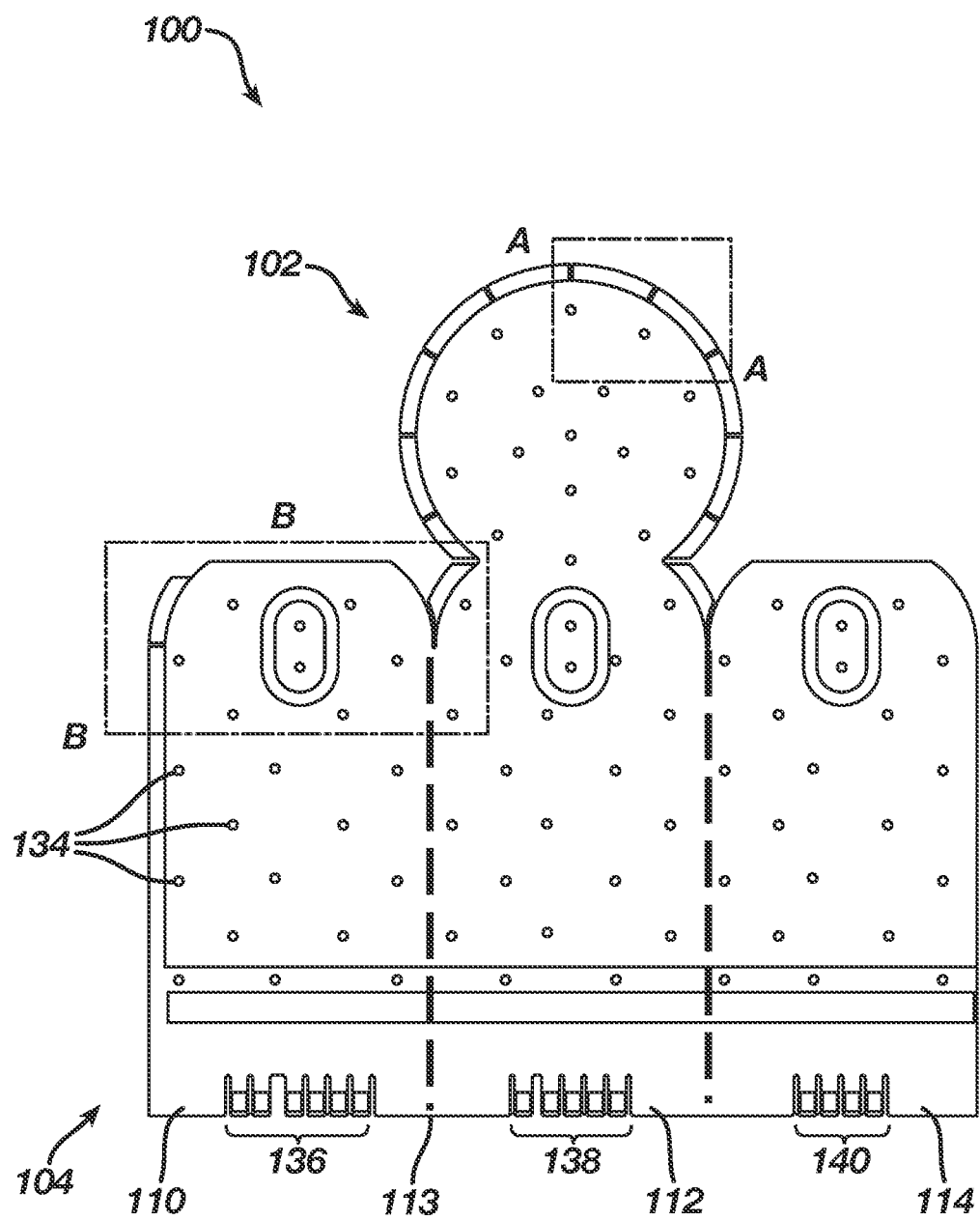
FIG. 2 depicts a planar substrate for forming a tip of this disclosure.

The surface of flexible circuit 100 visible in FIG. 2 becomes the inner surface of flexible circuit 200. Flexible circuit 100 may include various segments depending on the desired structure of the flexible circuit 200. As seen in FIG. 2, flexible circuit 100 has a first segment 102 and a second segment 104. First segment 102 may have a circular shape and second segment 104 may have a generally rectangular shape with one or more spaces along its upper edge adjoining segment 102 when in the planar configuration. Flexible circuit 100 may be formed into the flexible circuit 200 reflected in FIGS. 5-6, with first segment 102 becoming the distal-most portion (base of the cylinder) 202 of flexible circuit 200 and with segment 104 becoming a lateral surface (wall of the cylinder) 204 of flexible circuit 200. Segment 102 may be provided as having a rounded pattern (e.g., circular, elliptical or otherwise curved).

Segment 104 may include a plurality of sections or sectors, such as first sector 110, second sector 112, and third sector 114. Dashed lines 113 are provided on second segment 104 demarcating boundaries between these sectors. Each sector 110, 112, 114 can include a plurality of selectively positioned irrigation ports 134 to provide irrigation out of flexible circuit 200. Ports 134 can be created in any manner of fabrication techniques (e.g., via laser drilling). Solder regions 136, 138 and 140 may also be provided on second segment 104, with region 136 on first sector 110, region 138 on second sector 112, and region 140 on third sector 114, each having various contacts in conductive communication (operatively coupled) with the electronic componentry disposed on the corresponding sector. In some examples as depicted, region 136 can have six (6) contacts, region 138 can have five (5) contacts, while region 140 can have four (4) contacts. However, each region can have more or fewer contacts as needed or required In some examples, contacts of region 136, 138, 140 can be operatively coupled to thermocouples, and conductor elements of the system. In this manner, the electronic componentry on one of the three sectors 110, 112, 114 of second segment 104 may be controlled (e.g., for providing ablation or detecting electronic signals from tissue) and monitored separately (e.g., detecting separate temperatures for the separate temperature sensors disposed on each section of segment 104) from the electronic componentry of the system. Further, temperatures may be precisely monitored about flexible circuit 200 because each of sectors 110, 112, 114 includes two distinct temperature sensors, for a total of six temperature sensors on flexible circuit 200.

In some examples, spacing may be provided between sectors 110, 112, 114. The spacing may be provided through each layer, i.e., through the entire thickness of flexible circuit 100. However, this spacing may be provided through only the layers comprising conductive materials and need not be provided in the substrate and insulating layers comprising non-conductive materials. This spacing may, for example, be provided along the contours identified by the lines 113 and can segregate the various sectors 110, 112, and 114 from each other, for example, helping to prevent distribution of heat from one sector to the other. Furthermore, sectors 110, 112, 114 can include portions 109 (see FIG. 4) that in flexible circuit 200, are positioned in zone 203 adjacent the base 202. In some examples, insulative materials may be disposed within the spacing.

Figure 3:
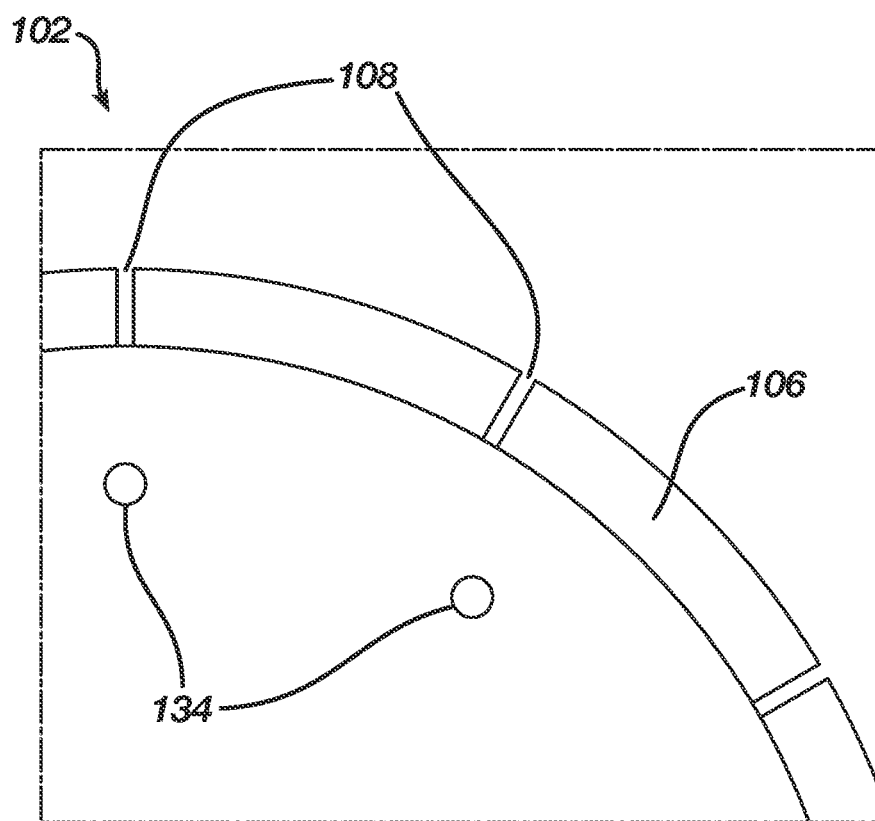
FIG. 3 depicts a close-up view of section A-A of FIG. 2 showing certain features of the first segment.

Turning to FIG. 3, segment 102 comprises spaces 108 between pedals 106 radially positioned about segment 102 that can accommodate a transition zone 203 between base 202 and wall 204. Ports 134 may further be provided through first segment 102.

Figure 4:
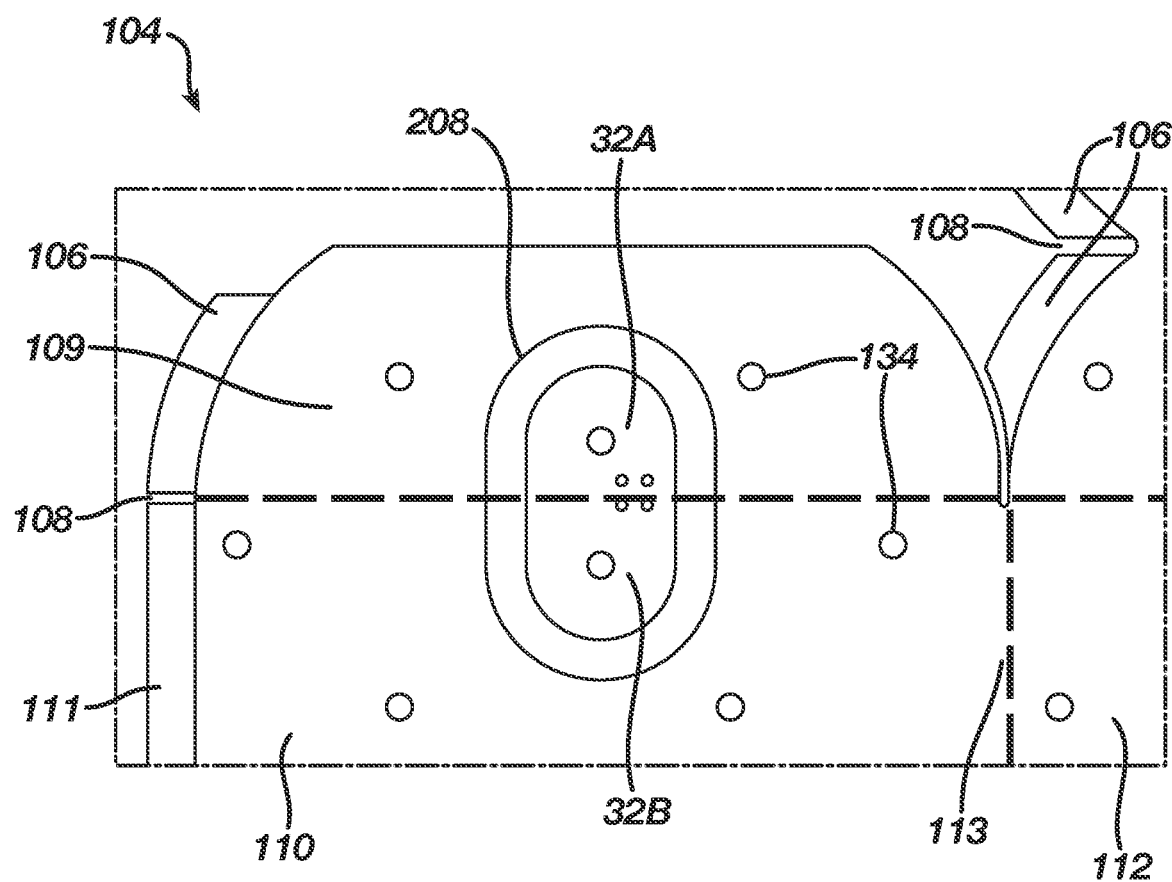
FIG. 4 depicts a close-up view of section B-B of FIG. 2 showing certain features of second segment.

Turning to FIG. 4, a close-up of section B-B is showing segment 104 with spaces 108 between pedals 106 and lower tab 111 of respective sectors 110 and 114. It is noted that sector 112 does not have a lower tab 111 since it comprises sectors 110, 114 on both of its lateral side edges. Instead, sector 112 has two upper pedals 106 adjacent what will become transition zone 203. Holes 208 may be provided in sectors 110, 112, 114 that are centrally positioned in the respective sector as well as positioned so that the electrode 32 of each respective sector 110, 112, and 114 can be arranged in both the transition zone 203 and wall 204. Stated differently, sectors 110, 112, 114 collectively are structured to accommodate transition zone 203 between base 202 and wall 204 that includes upper portion 32A of electrode 32 while lower portion 32B is positioned in the wall 204. In some examples, holes 208 may be positioned at least partially within both wall 204 and transition zone 203. Holes 208 may accommodate various electronic components of the catheter, e.g., electrodes 32.

Figure 5:
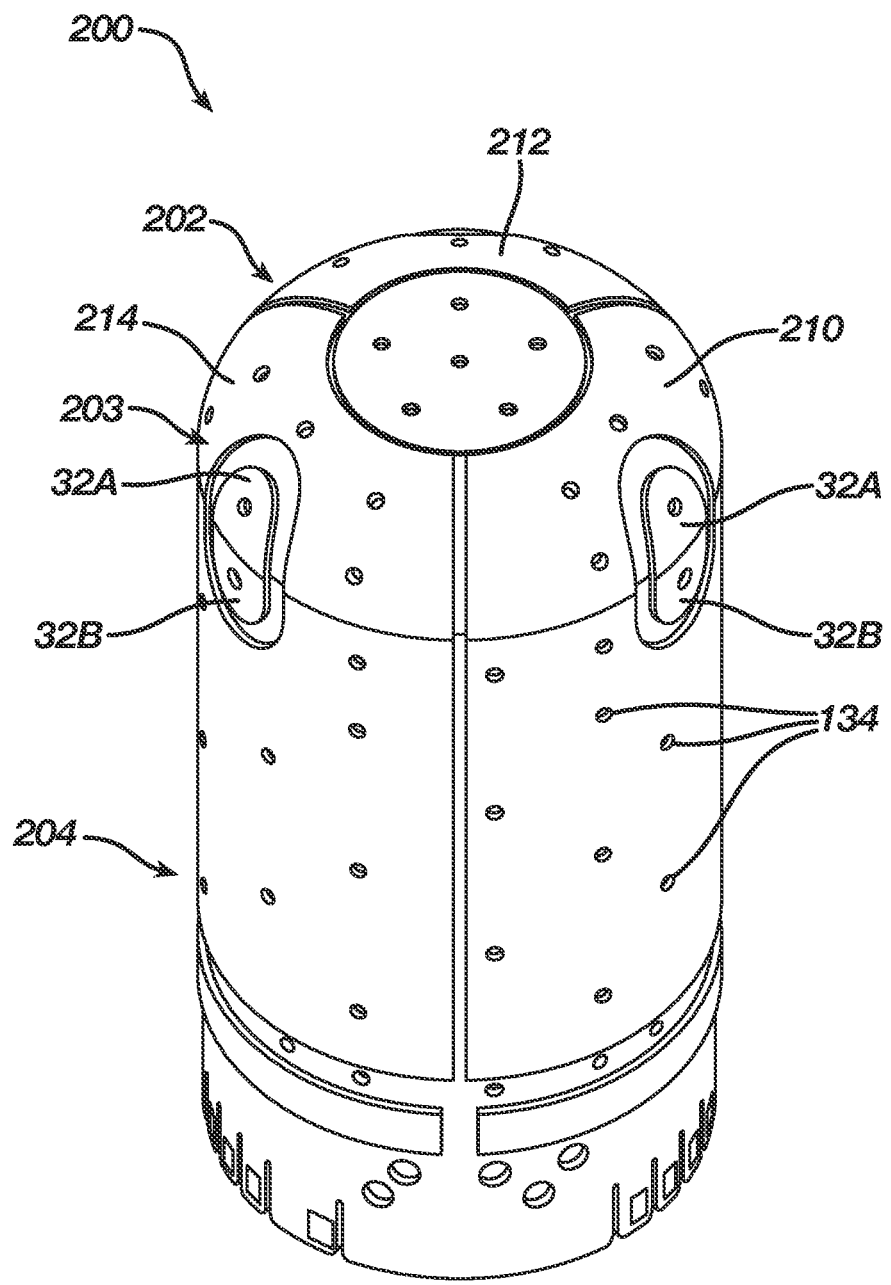
FIG. 5 depicts a close-up view of a tip of this disclosure.
Figure 6:
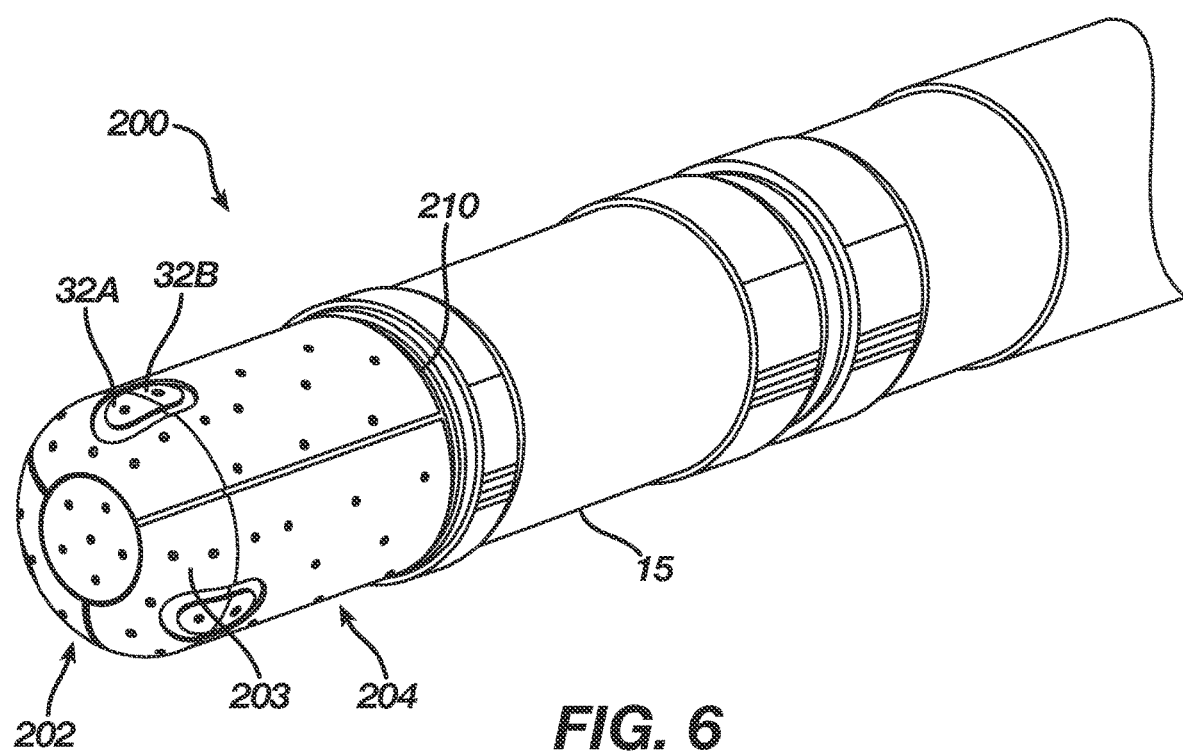
FIG. 6 depicts the flexible circuit of FIGS. 2-4 formed into a flexible-circuit tip and connected to a distal end of a catheter.

Previously described flexible circuit 100 may be formed into flexible circuit 200 shown in FIG. 5 and connected to distal end 15 of catheter body 14, as shown in FIG. 6. Catheter body 14 may be disposed longitudinally therethrough with at least two lumens. For example, one of the two lumens may be used to conduct irrigation fluid through catheter body 14 and into flexible circuit 200. The other lumen may contain lead wires for conveying signals, e.g., electrical signals, to and from the electronic componentry of flexible circuit 200. Additional lumens may be provided to, e.g., enable steering functionality, such as by including puller wires, or for a guide wire, as is known in the art. Flexible circuit 200 can be seen including sectors 210, 212, and 214, each which correspond to the three sectors 110, 112, and 114, respectively.

Turning to FIG. 6, upon forming flexible circuit 100 into flexible-circuit flexible circuit 200, a space may be formed between first sector 210 and third sector 214. This space may be filled with an insulating material for the spaces between first sector 110 and second sector 112 and between second sector 112 and third portion 114. Catheter body 14, outfitted with flexible circuit 200 thus provides various improvements in catheter tip design. Notably, rather than positioning microelectrodes on the lateral wall of flexible circuit 200, electrodes 32 (including upper and lower portions 32a, 32b) are positioned in on the distal radius at least partially on the dome and later wall of flexible circuit 200 to optimize signal collection. In prior approaches, electrodes 32 being positioned only on the lateral wall 204 were discovered to be less likely to have direct contact with tissue in a perpendicular or diagonal contact with tissue due to electrode location. The herein disclosed solutions resolves this by maintaining conductivity while also optimizing the location of electrodes 32.

Moreover, the electrodes of flexible circuit 200 in one of sectors 210, 212, 214 can be activated or deactivated separately from the electrodes on each of the other sectors, and they can be activated to provide different functionality, e.g., ablation or ECG sensing. Further, the electrical signals, typically in the RF range of the generator, provided to each of the three sectors may be the same or different than the electrical signals provided to one or both of the others. That is, the power delivered to each tip sector (e.g., power amount denoted in Watts) can be the same or different for each of the sectors. For example, the power amount delivered to the first tip sector ("first power amount" in Watts) can be controlled to be different (i.e., higher or lower) than the power amount delivered to the second tip sector ("second power amount"). As well, the third tip sector can be turned off or a third power amount can be provided to the third tip sector ("third power amount") that is different from the first power amount or the second power amount. Alternatively, energy delivered (in Joules) to each sector can be the same or different for each sector. In yet another example, the frequency of the RF signals provided to one sector may be varied relative to the frequency of the signals provided to one sector or both other sectors. The RF signals may be varied to any frequency within the RF frequency band of 10 kHZ to 1 MHz, e.g., based on suitable feedback controls. Such techniques to control energy or power to the tip sectors assist in controlling the temperature of flexible circuit 200 or tissue being ablated, and may further assist in improving the precision of the ablation.

Figure 7:
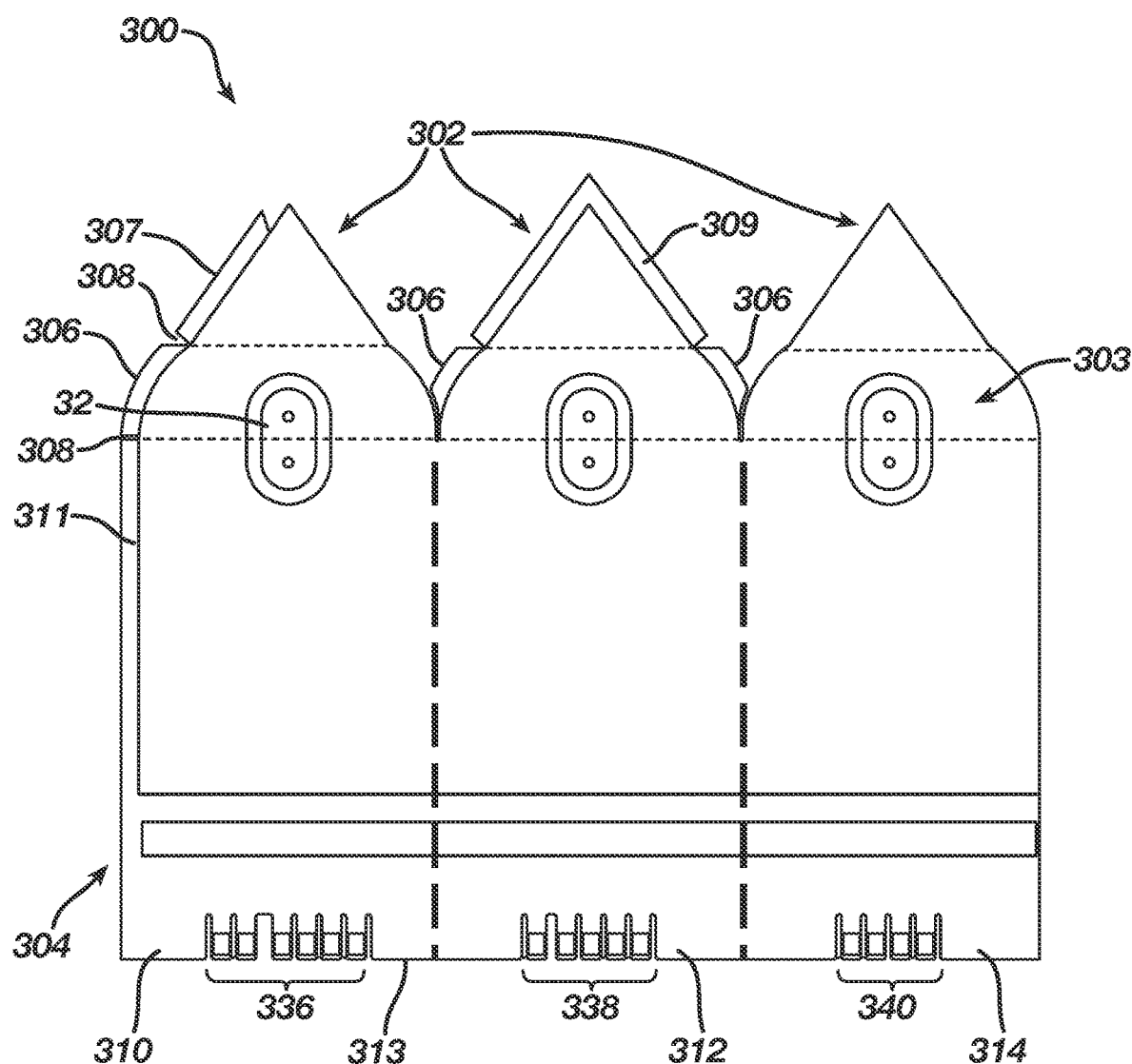
FIG. 7 depicts a planar substrate for forming another tip of this disclosure.

FIG. 7 reflects an alternative flexible circuit 300 that may be employed within a catheter, such as catheter 14, to provide signals concerning location and force to a processor in console 24. Flexible circuit 300 includes a substantially planar substrate with a first segment 302 and a second segment 304. First segment 302 may be positioned at or adjacent the transition zone and base sections of flexible circuit 300 and be formed with one or more angled edges that meet at an apex to form a triangular shaped distal end of flexible circuit 300, similar to the function of previously described segment 102. Rather than having a central cap area of segment 102 of flexible circuit 100, flexible circuit 300 has three (3) sectors 310, 312, 314 that form sections of a pie with overlapping tabs.

In particular, segment 304, similar to prior segment 104, can be formed into a lateral wall of the non-planar tip associated with flexible circuit 300. Segment 304 may include a plurality of sections or sectors, such as first sector 310, second sector 312, and third sector 314. Dashed lines 313 are provided on second segment 304 demarcating boundaries between these sectors. Similar to flexible circuit 100, solder regions 336, 338 and 340 may also be provided with second segment 304.

Also similar to segment 104, segment 304 comprises spaces 308 between pedals 306, 307 positioned in the transition zone as well as adjacent the upper most tab 307 end at the flexible electrode 300 (i.e. top of the triangular shaped point) and lower tab 311 of respective sectors 310 and 312. It is noted that sectors 312 and 314 do not have lower tabs 311. Instead, sector 312 has two upper pedals 306 adjacent what will become transition zone 303 along with a single pedal that wraps around the upper most apex of sector 312 and extends partially down each adjoining edge extended from said apex. Between tabs 306, 309 of sector 312 it can be seen that space 308 is provided.

Sectors 310, 312, 314, similar to those of flexible circuit 100, may have holes associated with each electrode that are centrally positioned in the respective sector as well as positioned so that the electrode 32 of each respective sector 310, 312, 314 can be arranged in both the transition zone 303 and wall once in the nonplanar configuration. Stated differently, sectors 310, 312, 314 collectively are structured to accommodate transition zone 303 between the base and lateral side wall of the flexible circuit. In some examples, holes associated with electrodes 32 may be positioned at least partially within the lateral side wall and transition zone.

Figure 8:
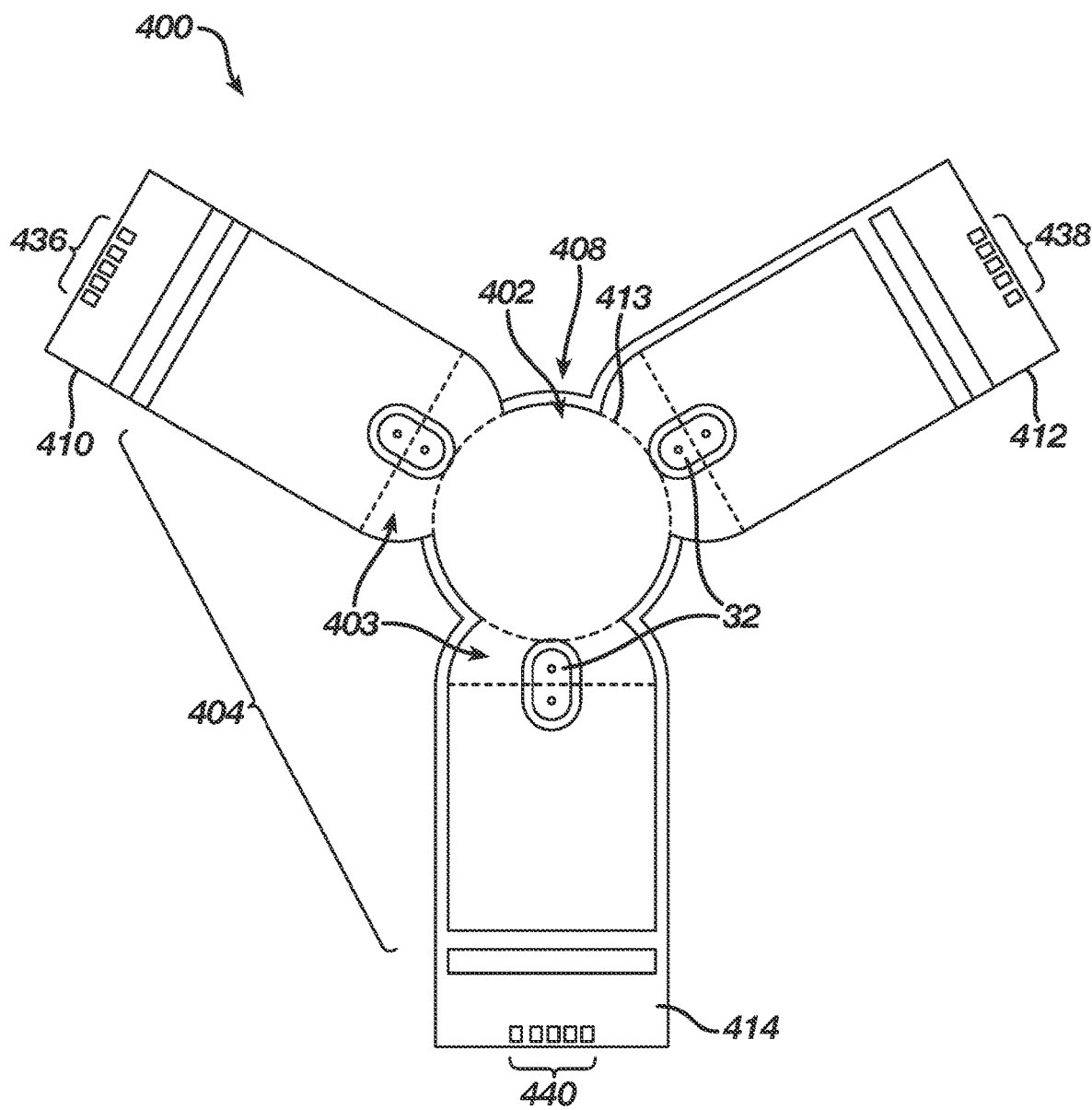
FIG. 8 depicts a planar substrate for forming another tip of this disclosure.

FIG. 8 reflects an alternative flexible circuit 400 that may be employed within a catheter, such as catheter 14, to provide signals concerning location and force to a processor in console 24. Flexible circuit 400 includes another substantially planar substrate with a first segment 402 and a second segment 404 that includes a plurality of petal sectors 410, 412, 414. First segment 402, similar to segment 102, may have a circular shape while being positioned at or adjacent the transition zone and base sections of flexible circuit 400. Segment 402 may be provided as having a rounded pattern (e.g., circular, elliptical or otherwise curved).

Segment 402 being centrally positioned with its curved shape acts as a central punch with segment 404 having its petal sectors 410, 412, 414 that fold proximally to form the distal radii and cylinder walls of flexible circuit 400 when in the nonplanar configuration. Segment 404 form the lateral wall of the non-planar flexible circuit associated with flexible circuit 400 and extend outward from segment 402. Petal sectors 410, 412, 414 can be seen radially separated about segment 402. In some examples, sectors 410, 412, 414 are equally spaced as shown with space 408. Spaces 408 can be positioned adjacent the transition zone 403 as well as adjacent segment 402.

Dashed boundary lines 413 are provided in FIG. 8 strictly to depict the demarcation between segment 402 and sectors 410, 412, 414, about which each sectors 410, 412, 414 can be folded and then attached together to form the walls and base of the nonplanar flexible circuit associated with flexible circuit 400. Similar to flexible circuits 100, 300, solder regions 436, 438 and 440 may also be provided with at the bottom edge of sectors 410, 412, 414, respectively. Sectors 410, 412, 414, similar to those of flexible circuits 100, 300, may have holes associated with each electrode that are centrally positioned in the respective sector as well as positioned so that the electrode 32 of each respective sector 410, 412, 414 can be arranged in both the transition zone 403 and wall once in the nonplanar configuration.

Substrates used to form the flexible circuits described in this disclosure may be a single layer. Alternatively, it may include between two and ten layers, e.g., four layers. Each layer is identical to the others, including the shapes of the various portions and segments described above. However, thickening by layers results in increased non-linearity of signal yield. An advantage that a thinner substrate (e.g., four layers) has over a thicker substrate (e.g., eight layers) is that it is easier to deform or bend, which is helpful for assembling flexible circuit to other catheter components and ultimately for fitting it within the inner-diameter envelope of the catheter, as will be detailed below.

It is noted that the make-up of biological tissue (e.g., water content, thickness or other tissue characteristics) in contact with a flexible circuit sector can affect the resistivity and therefore the RF power being delivered by that flexible circuit sector to the tissue. As such, the amount of temperature rise in that flexible circuit sector due to the energy or power delivered to such tissue can be different from other flexible circuit sectors in contact with the same tissue at different locations with correspondingly different tissues characteristics (or even different tissues). Therefore, one advantage of the embodiments herein is the ability for the system to deliver different power levels to different flexible circuit sectors to ensure that the temperature measured for one flexible circuit sector is generally the same for all of the flexible circuit sectors.

Flexible circuit 200 (or 300 or 400) may be brought into contact with tissue such that the tissue contacts at least a portion of the first sector, or at least a portion of the first sector and at least a portion of a second sector, or at least a portion of each of the three sectors. ECG signals may be separately assessed by the various electrodes of the three sectors such that the user or the system can determine which sectors contact tissue to determine which electrodes to activate to ablate. Further, the sector-specific signals of ECG may be used to tailor the therapy. For example, while sector 210, operating as an electrode such as an ablation electrode, a sensor electrode, and/or a recording electrode, provides energy to tissue that sector 210 (or at least a portion thereof) contacts, the temperature sensors on sector 210 can measure and provide temperature data to processor 22.

Simultaneously, some or all of the temperature sensors on flexible circuit 200 may provide temperature data to processor 22, while sectors 212 and 214, operating as electromagnetic sensors and not in contact with tissue, in partial contact with tissue, or in full contact with tissue, may provide ECG data to processor 22 or may be deactivated. Alternatively, one of sectors 212 or 214 may be deactivated while the other provides ECG data. That is, while one or two sectors' electrodes function as ablation electrodes, the other electrodes can provide input to determine if additional areas should be ablated, and if so, how the therapy should be provided or tailored (e.g., via power modification, duration of activation, continuous or pulsed activations, etc.). Further, by providing ablation energy only to those sectors in contact with tissue, ablation energy may be precisely provided directly to tissue such that energy applied to blood may be minimized, which minimizes the likelihood of thrombus formation. In addition, with a smaller area of the anatomy (e.g., epicardial or renal) directly receiving the energy, there will be a higher probability that the errant tissue will be ablated faster and more accurately. Further, the ECG data from non-tissue contacting sector(s) may be used to check for early signs of blockages (e.g., thrombi), while tissue-contacting sector(s) in contact with tissue are being ablated, such that remedial steps may be promptly taken.

Additionally, in certain instances, e.g., when at least a portion of sectors of a flexible circuit (e.g., 210, 212, 214) is determined to be in contact with tissue, processor 22 may control the application of ablation energy, either automatically or based on user input, such that the ablation energy may be provided to tissue via all three sectors simultaneously or in succession. When the ablation energy is applied in succession to more than one electrode, the ablation electrodes may be activated one at a time or two at a time. Two exemplary in-succession activations include: 1) sector 210 may be activated then deactivate, then sector 212 may be activated then deactivated, and sector 214 may be activated then deactivated; and 2) sectors 210 and 212 may be activated, then sector 210 may be deactivated and sector 214 activated, then sector 212 may be deactivated and sector 210 activated. Additional in-succession activations in differing combinations may be performed and also repeated until the desired ablation is achieved, as indicated by ECG signals or other signals provided by the electrode. One advantage of in-succession activations is that it permits different portions of tissue to be ablated and monitored without moving the catheter. Further, in-succession activations may be combined with simultaneous activations of all of the sectors. Moreover, the activations, whether in sequence or simultaneous, may be performed repeatedly.

Figure 9:
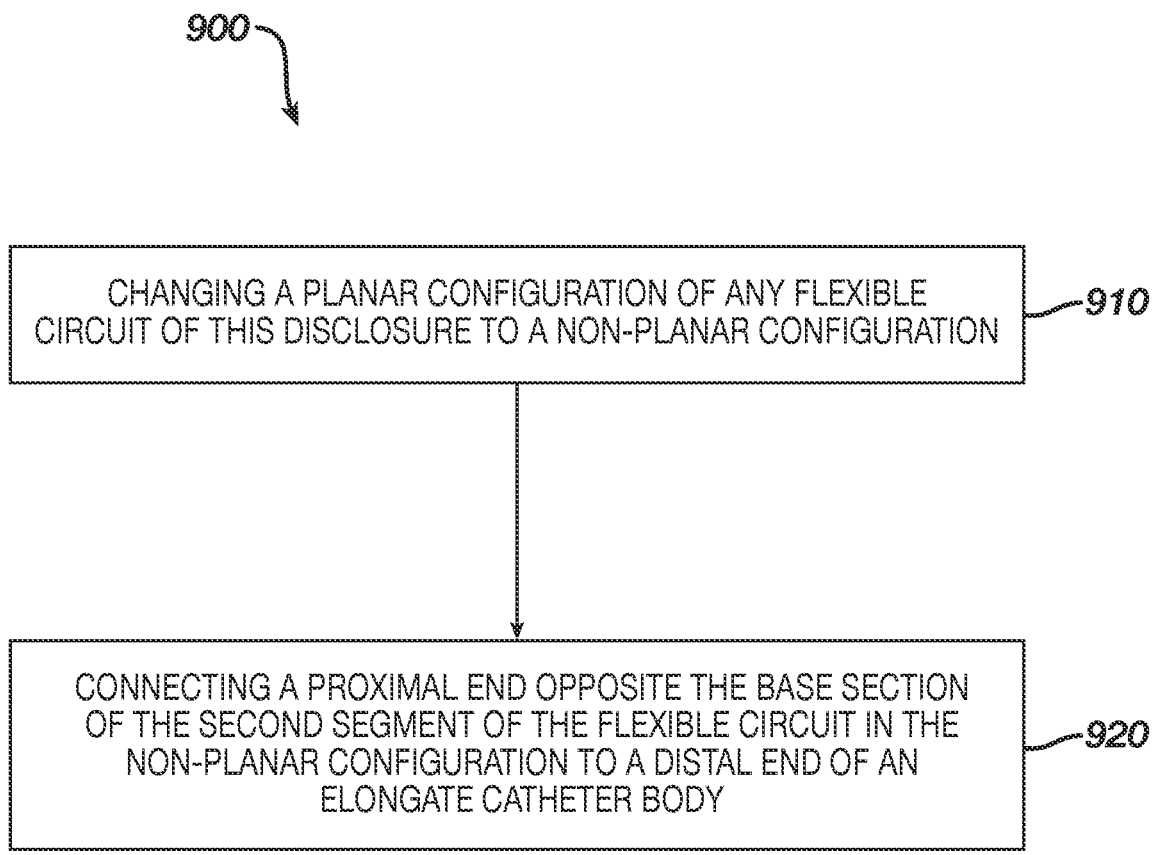
FIG. 9 is a flow diagram illustrating an example method of ablating tissue.

FIG. 9 is a flow diagram illustrating an example method 900 for assembling a catheter. The method 900 can include step 910 changing a planar configuration of any flexible circuit of this disclosure to a non-planar configuration. Step 920 can include connecting a proximal end opposite the base section of the second segment of the flexible circuit in the non-planar configuration to a distal end of an elongate catheter body.

Figure 10:
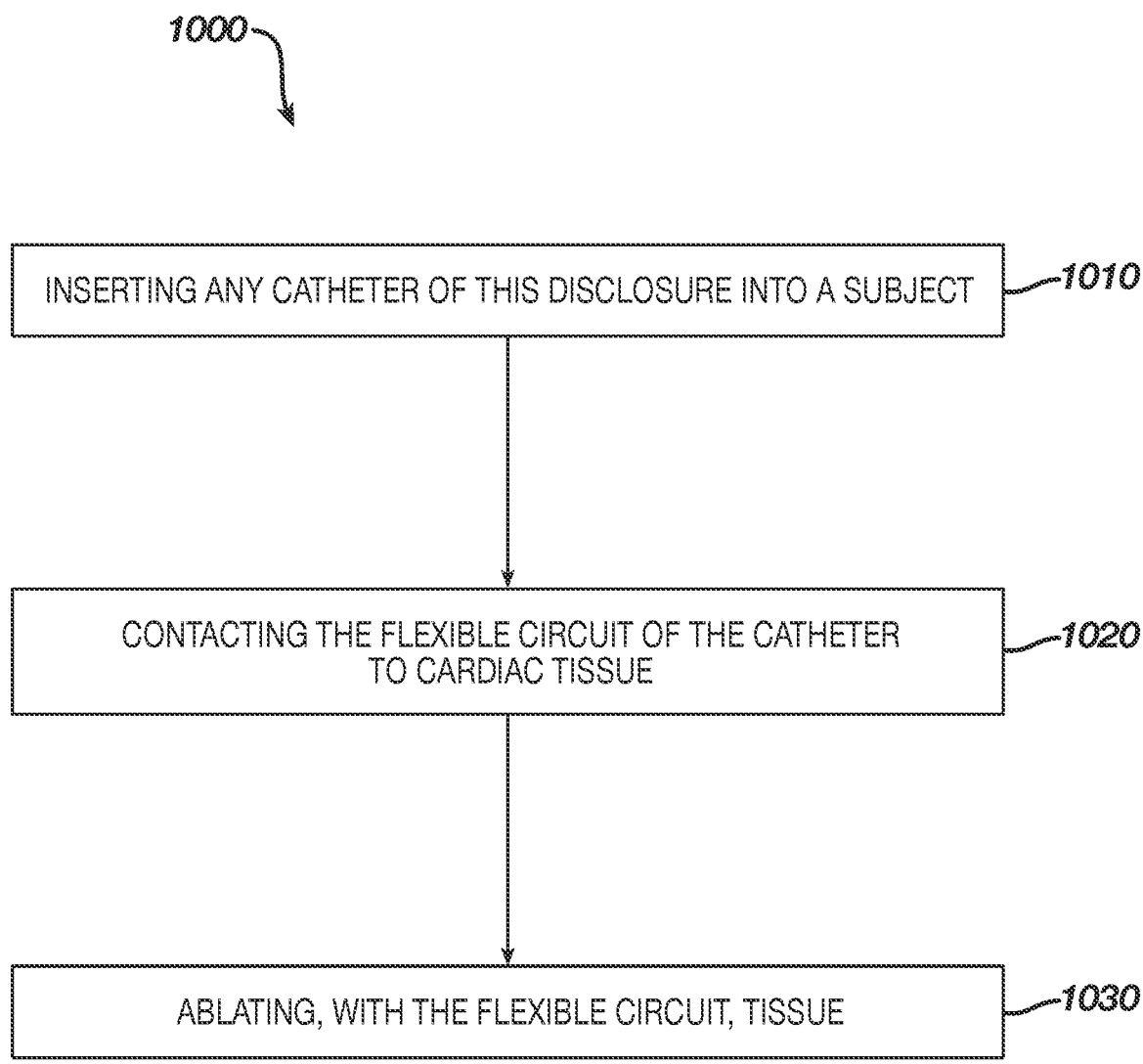
FIG. 10 is a flow diagram illustrating an example method of ablating tissue.

FIG. 10 is a flow diagram illustrating an example method 1000 of ablating tissue. The method 1000 can include step 1010 inserting any catheter according to this disclosure into a subject. Step 1020 can include contacting the flexible circuit of the catheter to cardiac tissue. Step 1030 can include ablating, with the flexible circuit, tissue.

In some epicardial applications, certain design considerations may suggest further minimizing heat generated by one sector from being detected by a thermocouple of another sector, and further minimizing the likelihood that ECG signals detected by an electrode on one sector are also detected by a sensor of another sector. Accordingly, one or two of the three sectors may be fabricated with greater insulation properties but without other functions, such as temperature measurement, ablation, and sensing, and associated componentry, such as thermocouples and electrodes. Accordingly, one or two of the sectors, e.g., sector 212, sector 214, or both, may have a greater amount of insulation material incorporated therein than in those embodiments where these sectors include functions of, e.g., ablation. Thus, for example, a ceramic material may be deposited onto flexible circuit 100 over sectors 112 and 114, which assists in preventing heat from ablated tissue from affecting the catheter tip via these sectors.

As noted above, ECG signals may be separately assessed by electrodes disposed on the flexible circuit such that the user or the system can determine that the flexible circuit contacts tissue, and, in those embodiments with electrodes on different flexible circuit sectors, to determine which electrodes to activate for providing ablation therapy. Contact with tissue may also be determined using force contact sensors, e.g., as described in U.S. patent application Ser. No. 15/452,843, filed Mar. 8, 2017, which is incorporated by reference herein in its entirety. A contact force sensor particularly suited for use in a catheter having a split tip is now described, and also described in U.S. patent application Ser. No. 16/036,710, filed Jul. 16, 2018, and incorporated by reference herein in its entirety.

The flexible circuit, in any of the foregoing embodiments, may be included on a distal end of a catheter. The catheter may also include an elongate body having at least two lumens disposed longitudinally therethrough. A core may be attached to the distal end of the catheter, at least a portion of which may be disposed within the second segment of the flexible circuit. The core may comprise an insulative material, such as polyurethane. Further, the core may include a lumen oriented transverse to a longitudinal axis of the core. A second insulation material may be disposed between the second segment and the core. The core may be in communication with a first one of the at least two lumens of the catheter body such that fluid may flow through one of the lumens and through the core. A plurality of wires may be disposed within at least a second one of the at least two lumens and this plurality of wires may be electrically connected to the flexible-circuit.

The catheter may be used according to the following method and variations. First, the catheter may be inserted into a subject, e.g., a human subject, proximate to the subject's heart. The flexible circuit may be maneuvered into contact with the tissue. The catheter may be an aspect of an ablation system that also includes a processor that is in communication with the flexible circuit. The first sector may monitor an ECG signal and provide the signal to the processor. The second sector may monitor an ECG signal and provide the signal to the processor. The third sector may monitor an ECG signal and provide the signal to the processor. Each of the three sectors may also measure temperature and provide temperature data to the processor. Ablation energy may be provided to the flexible circuit, e.g., as controlled by the processor.

An electrode can be included with the flexible circuit having at least one flexible printed circuit board (PCB) that is bonded, by an adhesive, to a supporting metallic sheet. The flexible PCB comprises a flexible thermally-insulating substrate comprising an outer surface that is coated by an outer layer of an electrically-conducting (and biocompatible) metal, such as gold, palladium, or platinum, and an inner surface that is coated by an inner layer of the same (and/or another) thermally-conducting metal. The inner surface may further support one or more electric components such as sensors (e.g., thermocouples) and traces, which are electrically isolated from the inner thermally-conducting layer. Following the deposition of the electric components, the coating of the substrate, and the bonding of the PCB to the supporting sheet, the flexible PCB (together with the supporting sheet) may be deformed into any suitable shape.

What is claimed is:

1. A flexible circuit for use with a catheter tip, comprising:
a first segment comprising a base section;
a second segment comprising a lateral wall section;
a transition section between the base section and lateral wall sections, the transition section being at least partially positioned adjacent a shared region of the base section and lateral wall sections; and
one or more electrode regions comprising a respective electrode, the one or more electrode regions being positioned at least partially in the transition section and the second segment;
the second segment being generally rectangular when oriented in a planar configuration prior to being in a non-planar configuration when used with the catheter tip and further comprising:
a first sector, a second sector, and a third sector, each sector comprising a respective electrode region comprising an electrode, the respective electrode region being positioned at least partially in the transition section and the respective sector;
the first segment comprising a plurality of triangle shaped sectors formed continuous with the first, second, and third sectors, respectively, of the second segment; and
each sector of the second segment comprising a rounded or curved upper edge that tapers from an upper edge of the respective sector of the second segment towards an apex of a respective triangle shaped sector of the plurality of triangle shaped sectors.

2. The flexible circuit of claim 1, the respective electrode of the one or more electrode regions being an ablating electrode.

3. The flexible circuit of claim 1, the respective electrode of the one or more electrode regions being a recording electrode.

4. The flexible circuit of claim 1, the respective electrode of the one or more electrode regions being a sensing electrode.

5. The flexible circuit of claim 1, the first segment being generally planar when oriented in a planar configuration prior to being in the non-planar configuration when used with the catheter tip.

6. The flexible circuit of claim 1, the second sector being positioned between the first and third sectors and formed continuous with the first segment along an adjoining region.

7. The flexible circuit of claim 1, wherein the rounded or curved upper edge of the first, second, and third sectors form a dome-like shape to the transition section when the flexible circuit is in the non-planar configuration.

8. The flexible circuit of claim 1, wherein the base section is collectively formed by the plurality of triangle shaped sectors.

9. The flexible circuit of claim 1, wherein at least one of the triangle shaped sectors of the plurality of triangle shaped sectors comprises:
a first layer comprising a substrate; and
a second layer comprising:
a first upper petal adjacent an upper edge and the transition section; and
a lower tab spaced apart from the first upper petal and extended substantially downward along a lateral edge of the respective sector.

* * * * *